US012697506B2

(12) United States Patent
Kuusela

(10) Patent No.: US 12,697,506 B2
(45) Date of Patent: Aug. 4, 2026

(54) RADIATION TREATMENT PLAN OPTIMIZATION AS A FUNCTION OF BOTH DOSIMETRIC AND NON-DOSIMETRIC PARAMETERS

(71) Applicant: Siemens Healthineers International AG, Steinhausen (CH)

(72) Inventor: Esa Kuusela, Espoo (FI)

(73) Assignee: Siemens Healthineers International AG, Steinhausen (CH)

( * ) Notice: Subject to any disclaimer, the term of this patent is extended or adjusted under 35 U.S.C. 154(b) by 848 days.

(21) Appl. No.: 18/076,580

(22) Filed: Dec. 7, 2022

(65) Prior Publication Data
US 2024/0189622 A1     Jun. 13, 2024

(51) Int. Cl.
*A61N 5/10*          (2006.01)

(52) U.S. Cl.
CPC ........... *A61N 5/103* (2013.01); *A61N 5/1031* (2013.01)

(58) Field of Classification Search
CPC .............................. A61N 5/103; A61N 5/1031
See application file for complete search history.

(56) References Cited

U.S. PATENT DOCUMENTS

| | | |
|---|---|---|
| 2015/0335914 A1 | 11/2015 | Otto |
| 2020/0398080 A1* | 12/2020 | Ruokokoski ......... A61N 5/1031 |
| 2021/0020297 A1 | 1/2021 | Adler |
| 2021/0299469 A1 | 9/2021 | Harju |

OTHER PUBLICATIONS

International Search Report from related Application No. PCT/EP2023/082874 dated Feb. 16, 2024; 5 pages.

* cited by examiner

*Primary Examiner* — Chih-Cheng Kao
(74) *Attorney, Agent, or Firm* — Fitch, Even, Tabin & Flannery LLP

(57)          ABSTRACT

A control circuit optimizes a radiation treatment plan as a function of a plurality of different criteria that include both dosimetric parameters and non-dosimetric parameters. By one approach, during a first optimization phase, the control circuit generates a first phase optimized radiation treatment plan as a function of dosimetric parameters (for example, as a function of only dosimetric parameters). Then, during a second optimization phase, the control circuit generates a second phase optimized radiation treatment plan as a function of the first phase optimized radiation treatment plan and at least one non-dosimetric parameter.

20 Claims, 2 Drawing Sheets

By A Control Circuit Configured To Optimize A Radiation Treatment Plan As A Function Of A Plurality Of Different Criteria That Include Both Dosimetric Parameters And Non-dosimetric Parameters 201 — During A First Optimization Phase, Generate A First Phase Optimized Radiation Treatment Plan As A Function Of Dosimetrical Parameters 202 — Determine An Allowance Parameter For Least One Of The Domestic Parameters To Provide At Least One Determined Allowance Parameter 203 — During A Second Optimization Phase, Generate A Second Phase Optimized Radiation Treatment Plan As A Function Of The First Phase Optimized Radiation Treatment Plan And At Least One Non-dosimetric Parameter 204 — During A Third Optimization Phase, Generate A Third Phase Optimized Radiation Treatment Plan As A Function Of The Second Phase Optimized Radiation Treatment Plan And At Least One Non-dosimetric Parameter

*200*

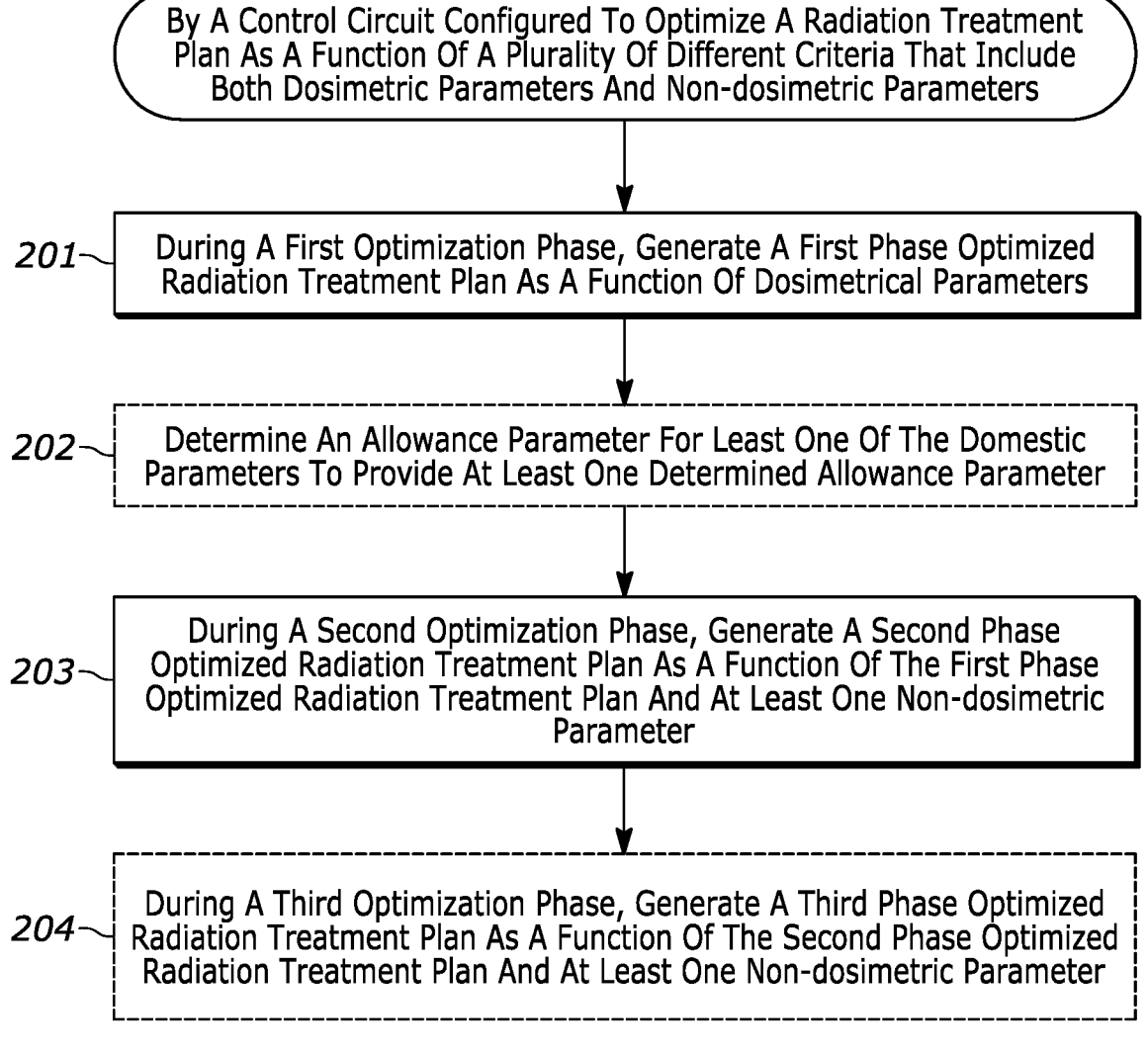

By A Control Circuit Configured To Optimize A Radiation Treatment Plan As A Function Of A Plurality Of Different Criteria That Include Both Dosimetric Parameters And Non-dosimetric Parameters 201 — During A First Optimization Phase, Generate A First Phase Optimized Radiation Treatment Plan As A Function Of Dosimetrical Parameters 202 — Determine An Allowance Parameter For Least One Of The Domestic Parameters To Provide At Least One Determined Allowance Parameter 203 — During A Second Optimization Phase, Generate A Second Phase Optimized Radiation Treatment Plan As A Function Of The First Phase Optimized Radiation Treatment Plan And At Least One Non-dosimetric Parameter 204 — During A Third Optimization Phase, Generate A Third Phase Optimized Radiation Treatment Plan As A Function Of The Second Phase Optimized Radiation Treatment Plan And At Least One Non-dosimetric Parameter

RADIATION TREATMENT PLAN OPTIMIZATION AS A FUNCTION OF BOTH DOSIMETRIC AND NON-DOSIMETRIC PARAMETERS

TECHNICAL FIELD

These teachings relate generally to treating a patient's planning target volume with energy pursuant to an energy-based treatment plan and more particularly to optimizing an energy-based treatment plan.

BACKGROUND

The use of energy to treat medical conditions comprises a known area of prior art endeavor. For example, radiation therapy comprises an important component of many treatment plans for reducing or eliminating unwanted tumors. Unfortunately, applied energy does not inherently discriminate between unwanted material and adjacent tissues, organs, or the like that are desired or even critical to continued survival of the patient. As a result, energy such as radiation is ordinarily applied in a carefully administered manner to at least attempt to restrict the energy to a given target volume. A so-called radiation treatment plan often serves in the foregoing regards.

A radiation treatment plan typically comprises specified values for each of a variety of treatment-platform parameters during each of a plurality of sequential fields. Treatment plans for radiation treatment sessions are often automatically generated through a so-called optimization process. As used herein, "optimization" will be understood to refer to improving a candidate treatment plan without necessarily ensuring that the optimized result is, in fact, the singular best solution. Such optimization often includes automatically adjusting one or more physical treatment parameters (often while observing one or more corresponding limits in these regards) and mathematically calculating a likely corresponding treatment result (such as a level of dosing) to identify a given set of treatment parameters that represent a good compromise between the desired therapeutic result and avoidance of undesired collateral effects.

In some cases, optimization proceeds as a function of multiple different criteria. Some criteria may relate directly to planned dose distribution while other features may relate to how the dose distribution is planned to be physically delivered. The applicant has determined that there is no readily intuitive way to compare changes with respect to the latter as regards the former. That situation, in turn, makes it difficult to define an optimization cost function in a manner that will correctly capture the intention of the planner in a variety of different cases.

By one approach, a planner must interactively adjust the weight of one or more non-dosimetric parameters during optimization to attempt to find a good balance between non-dosimetric parameters and dosimetric parameters. By another approach, a planner may employ a template value for the weight of a non-dosimetric parameter. Unfortunately, there is no guarantee that the latter approach will lead to a good balance in a given application setting. As an example of a successful balance, treatment time or fluence complexity may be drastically reduced with only an insignificantly small degradation in dosimetric plan quality.

BRIEF DESCRIPTION OF THE DRAWINGS

The above needs are at least partially met through provision of the method and apparatus for radiation treatment plan optimization as a function of both dosimetric and non-dosimetric parameters described in the following detailed description, particularly when studied in conjunction with the drawings, wherein:

FIG. 2 comprises a flow diagram as configured in accordance with various embodiments of these teachings.

Figure 1:
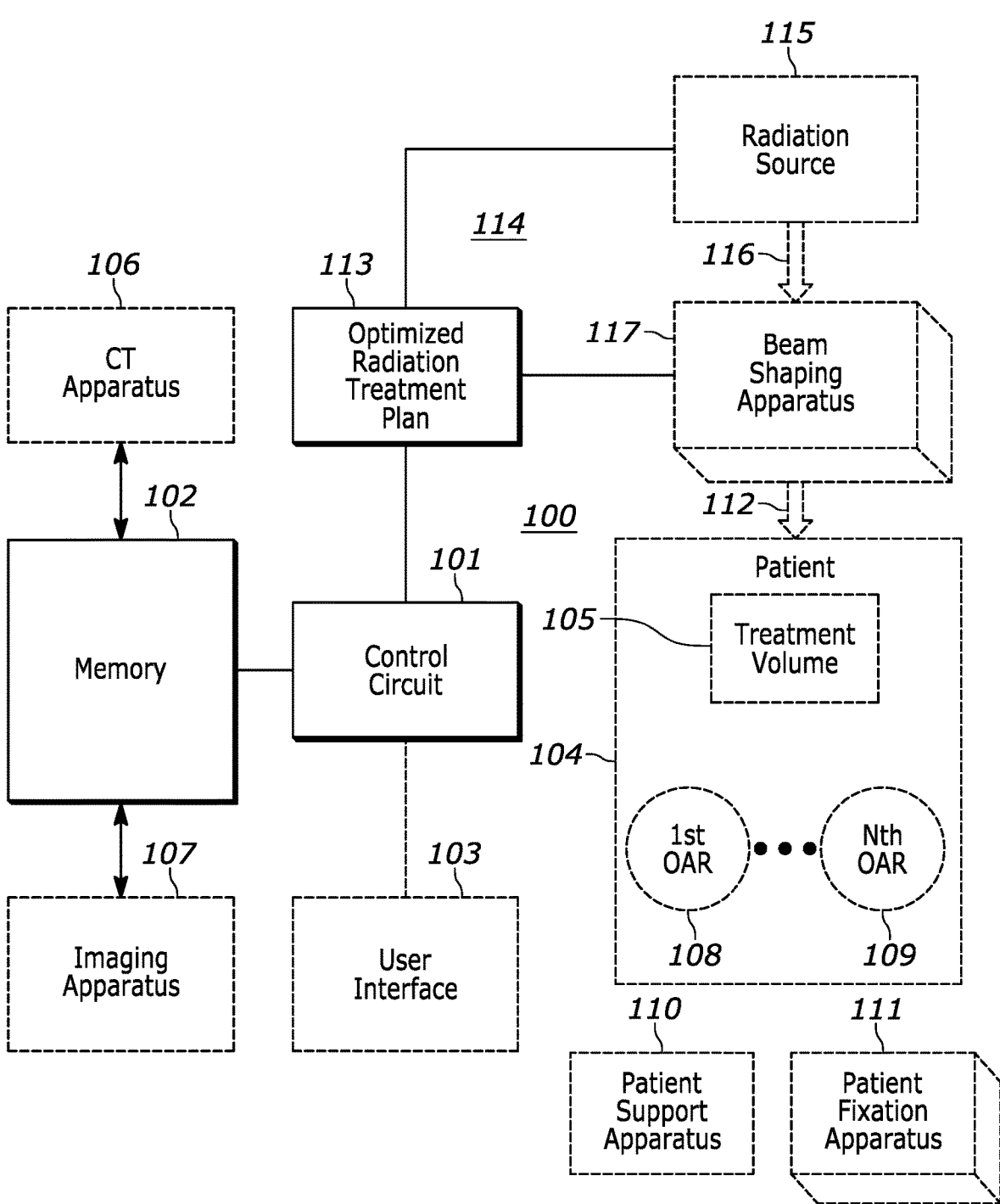
FIG. 1 comprises a block diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein. The word "or" when used herein shall be interpreted as having a disjunctive construction rather than a conjunctive construction unless otherwise specifically indicated.

DETAILED DESCRIPTION

Generally speaking, pursuant to these various embodiments a control circuit can be configured to optimize a radiation treatment plan as a function of a plurality of different criteria that include both dosimetric parameters and non-dosimetric parameters. By one approach, during a first optimization phase, the control circuit generates a first phase optimized radiation treatment plan as a function of dosimetric parameters (for example, as a function of only dosimetric parameters). Then, during a second optimization phase, the control circuit generates a second phase optimized radiation treatment plan as a function of the first phase optimized radiation treatment plan and at least one non-dosimetric parameter.

By one approach, the aforementioned dosimetric parameters may include dosing information for at least one of a target patient volume and an organ-at-risk. By one approach, the aforementioned non-dosimetric parameter(s) may include a parameter pertaining to at least one of time, fluence smoothness, monitor units, radiation treatment platform performance, and passing a quality assurance assessment.

By one approach, the aforementioned second optimization phase may comprise generating the second phase optimized radiation treatment plan as a function of the first phase optimized radiation treatment plan, the at least one non-dosimetric parameter, and also at least one dosimetric parameter. By one approach, the latter can comprise using all of the dosimetric parameters that were used during the first optimization phase.

These teachings are both practical and highly flexible in practice and will accommodate both variations to the foregoing and supplemental actions as well. As one example in these regards, these teachings will accommodate a third optimization phase that includes generating a third phase optimized radiation treatment plan as a function of the second phase optimized radiation treatment plan and at least one non-dosimetric parameter. For example, the latter non-dosimetric parameter may be different from any non-dosimetric parameters used during the aforementioned second optimization phase.

As another example of the flexibility of these teachings, these teachings will also accommodate determining an allowance parameter for at least one of the aforementioned dosimetric parameters to provide at least one resultant determined allowance parameter. In that case, generating the second phase optimized radiation treatment plan can comprise generating the second phase optimized radiation treatment plan as a function of the first phase optimized radiation treatment plan, the at least one non-dosimetric parameter, and the at least one determined allowance parameter. If desired, more than one allowance parameter can be determined, in which case generating the second phase optimized radiation treatment plan can include consideration of some or all of the plurality of determined allowance parameters. This approach allows a use of non-dosimetric parameters in a second phase of optimization in conjunction with an allowance constraint that prevents the dosimetric parameters from degrading too much from values achieved during the earlier phase of optimization. Accordingly, these teachings avoid a need for a user to assign or otherwise find weights for non-dosimetric parameters.

These and other benefits may become clearer upon making a thorough review and study of the following detailed description. Referring now to the drawings, and in particular to FIG. 1, an illustrative apparatus 100 that is compatible with many of these teachings will first be presented.

In this particular example, the enabling apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

The control circuit 101 operably couples to a memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to information such as optimization information, dosimetric parameters, and non-dosimetric parameters for a particular patient and information regarding a particular radiation treatment platform as described herein, this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as a dynamic random access memory (DRAM).)

By one optional approach the control circuit 101 also operably couples to a user interface 103. This user interface 103 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

If desired the control circuit 101 can also operably couple to a network interface (not shown). So configured the control circuit 101 can communicate with other elements (both within the apparatus 100 and external thereto) via the network interface. Network interfaces, including both wireless and non-wireless platforms, are well understood in the art and require no particular elaboration here.

By one approach, a computed tomography apparatus 106 and/or other imaging apparatus 107 as are known in the art can source some or all of any desired patient-related imaging information.

In this illustrative example the control circuit 101 is configured to ultimately output an optimized energy-based treatment plan (such as, for example, an optimized radiation treatment plan 113). This energy-based treatment plan typically comprises specified values for each of a variety of treatment-platform parameters during each of a plurality of sequential exposure fields. In this case the energy-based treatment plan is generated through an optimization process, examples of which are provided further herein.

By one approach the control circuit 101 can operably couple to an energy-based treatment platform 114 that is configured to deliver therapeutic energy 112 to a corresponding patient 104 having at least one treatment volume 105 and also one or more organs-at-risk (represented in FIG. 1 by a first through an Nth organ-at-risk 108 and 109) in accordance with the optimized energy-based treatment plan 113. These teachings are generally applicable for use with any of a wide variety of energy-based treatment platforms/apparatuses. In a typical application setting the energy-based treatment platform 114 will include an energy source such as a radiation source 115 of ionizing radiation 116.

By one approach this radiation source 115 can be selectively moved via a gantry along an arcuate pathway (where the pathway encompasses, at least to some extent, the patient themselves during administration of the treatment). The arcuate pathway may comprise a complete or nearly complete circle as desired. By one approach the control circuit 101 controls the movement of the radiation source 115 along that arcuate pathway, and may accordingly control when the radiation source 115 starts moving, stops moving, accelerates, de-accelerates, and/or a velocity at which the radiation source 115 travels along the arcuate pathway.

As one illustrative example, the radiation source 115 can comprise, for example, a radio-frequency (RF) linear particle accelerator-based (linac-based) x-ray source. A linac is a type of particle accelerator that greatly increases the kinetic energy of charged subatomic particles or ions by subjecting the charged particles to a series of oscillating electric potentials along a linear beamline, which can be used to generate ionizing radiation (e.g., X-rays) 116 and high energy electrons.

A typical energy-based treatment platform 114 may also include one or more support apparatuses 110 (such as a couch) to support the patient 104 during the treatment session, one or more patient fixation apparatuses 111, a gantry or other movable mechanism to permit selective movement of the radiation source 115, and one or more energy-shaping apparatuses (for example, beam-shaping apparatuses 117 such as jaws, multi-leaf collimators, and so forth) to provide selective energy shaping and/or energy modulation as desired.

In a typical application setting, it is presumed herein that the patient support apparatus 110 is selectively controllable to move in any direction (i.e., any X, Y, or Z direction) during an energy-based treatment session by the control circuit 101. As the foregoing elements and systems are well understood in the art, further elaboration in these regards is not provided here except where otherwise relevant to the description.

Referring now to FIG. 2, a process 200 that can be carried out, for example, in conjunction with the above-described application setting (and more particularly via the aforementioned control circuit 101) will be described. Generally speaking, this process 200 serves to facilitate generating an optimized radiation treatment plan 113 to thereby facilitate treating a particular patient with therapeutic radiation using a particular radiation treatment platform per that optimized radiation treatment plan. The following description also presumes, for the sake of an illustrative example, that the control circuit 101 is configured to optimize a radiation treatment plan as a function of a plurality of different criteria that include both dosimetric parameters and non-dosimetric parameters.

At block 201, this process 200 provides for, during a first optimization phase of the radiation treatment plan optimization process, generating a first phase optimized radiation treatment plan as a function of dosimetric parameters. Examples of relevant dosimetric parameters include, but are not necessarily limited to, dosing information for at least one of a target patient volume and an organ-at-risk. By one approach, this step comprises generating the first phase optimized radiation treatment plan as a function of only dosimetric parameters to the exclusion of any non-dosimetric parameters. By another approach, this step may include generating the first phase optimized radiation treatment plan as an additional function of one or more non-dosimetric parameters (such as a time-based non-dosimetric parameter).

By one optional approach, and as illustrated at optional block 202, this process 200 will accommodate determining an allowance parameter for at least one of the dosimetric parameters to thereby provide at least one determined allowance parameter. Depending upon the application setting, it may be beneficial to determine an allowance parameter for each of a plurality of some or all of the corresponding dosimetric parameters to thereby provide a plurality of determined allowance parameters. Generally speaking, and as will be described in more detail below, these determined allowance parameters specify and/or govern how far a dosimetric value that results from the first optimization phase can be thereafter varied as this process 200 continues.

At block 203, this process 200 provides for, during a second optimization phase that is subsequent to the aforementioned first optimization phase, generating a second phase optimized radiation treatment plan as a function of the first phase optimized radiation treatment plan and at least one non-dosimetric parameter. Generally speaking, this process 200 may create a new cost function to employ during the second phase optimization, wherein that new cost function is based on the solution derived by the first optimization phase.

Examples of potentially useful non-dosimetric parameters include, but are not necessarily limited to, time (for example, an amount of time required to administer radiation to the patient using the optimized radiation treatment plan), fluence smoothness (those skilled in the art will recognize "smoothness" as referring to the statistics/image processing-based processing of a given data set to create an approximating function that works to capture significant patterns within the data while not necessarily capturing noise or fine-scale structures and rapid phenomena; generally speaking, smoothness aims to offer a general idea of relatively slow changes of value with little attention being paid to closely matching the data values per se, and where smoothing methodologies typically have one or more associated tuning parameters that serve to control the extent of the smoothing), monitor units (where a monitor unit (MU) will be understood to comprise a measure of machine output from a clinical accelerator for radiation therapy such as a linear accelerator or an orthovoltage unit), radiation treatment platform performance, and/or passing (or failing) a quality assurance assessment.

It will be appreciated that this second optimization phase, which actively takes into account one or more non-dosimetric parameters, can yield successful results without having a user derive or assign any weights to any non-dosimetric parameters. In particular, such weighting can be automatically determined (or at least mimicked) based on the aforementioned allowance parameters. An illustrative example in these regards is provided below.

By one optional approach, the foregoing can be supplemented with at least one dosimetric parameter as well. In this case, this block 203 provides for generating a second phase optimized radiation treatment plan as a function of the first phase optimized radiation treatment plan, the at least one non-dosimetric parameter, and, in addition, at least one dosimetric parameter. By one approach, the at least one dosimetric parameter may be selected from the dosimetric parameters used during the first optimization phase. If desired, the second phase may include use of all of the dosimetric parameters that were used during the first optimization phase.

If desired, this process 200 will accommodate additional optimization phases that follow the aforementioned second optimization phase. FIG. 2 illustrates this possibility at optional block 204. During a third optimization phase, this process generates a third phase optimized radiation treatment plan as a function of the second phase optimized radiation treatment plan and at least one non-dosimetric parameter. By one approach, the latter non-dosimetric parameter may be different from any non-dosimetric parameter that was used during the second optimization phase.

Additional such optimization phases can be optionally employed as desired. To the extent additional optimization phases are utilized, those additional phases may again make use of a non-dosimetric parameter that was not utilized by any preceding optimization phases.

The resultant radiation treatment plan can then serve as the optimized radiation treatment plan 113 that the above-described radiation treatment platform 114 utilizes to deliver therapeutic radiation 112 to the patient 104.

Additional details will now be provided as regards the foregoing. It will be understood that these details are provided to serve an illustrative purpose and are not intended to suggest any limitations with respect to these teachings.

In this illustrative example, the aforementioned first optimization phase can be conducted by using any cost (or utility) function currently used in optimizers. For example, the cost function could be based on a weighted sum of quadratic terms. As another example, the cost function it can be a sum of piece-wise-linear functions (such as the so-called scorecard-based optimization). And as yet another example, the cost function can be based on a P(Q) function as is practiced in some prior art approaches.

Without losing any generality, this cost function can be expressed as $C_{dos}$ and its achieved value as $C_{dos}$. The optimal achieved dosimetric parameters can be denoted as $$\{q_{dos}^i\}.$$

Note that this first optimization phase can be done in dose-space, i.e., there is no need to find the machine control points to deliver this dose distribution, and it would be convenient (although not necessary) to consider that the cost can be calculated directly from the dose distribution, i.e. $C_{dos}(D): R^{n_d} \rightarrow R$, where D is the dose matrix that contains $n_d$ dose-calculation points.

In the second optimization phase a new cost function $C_{tot}$ can be created based on the solution found in the first optimization phase. By one approach, $C_{dos}$ is used to define the new cost function:

$$C_{tot}(F)=\Sigma_j w_j r_j(F)+G(C_{dos}(D(F)),c_{dos}+\delta c_{dos}),$$

where $r_j$ is the value of the j:th non-dosimetric parameters (which can be a direct function of the corresponding fluence pixel set or control point set F). The function G is a penalty function that has negligibly small values if the first argument is smaller than the second but which increases quickly after the first argument becomes larger than the second one. And parameter $\delta c_{dos}$ is a user specified allowance parameter indicating how far the dosimetric values are allowed to deviate from their initial values. There are multiple different ways how the penalty function G could be defined but one illustrative example is $$G(v, g) = \exp\left(\frac{v-g}{g}\right).$$

By another approach, each $$q_{dos}^i$$

could be penalized separately, each having its own allowance parameter.

By one approach, these teachings would accommodate handling the result from the first optimization phase as an actual optimization constraint. This could comprise, for example, having only the first term in the equation of $C_{tot}(F)$ shown above but accepting only solutions where $C_{dos}(D(F)) \leq c_{dos}+\delta c_{dos}$.

By one approach, the allowance parameter(s) may not actually be a "parameter" but instead might comprise a function of the cost function value or the dosimetric parameters to indicate, for example, situations where the allowance is not allowed (for example when a certain clinical goal is only barely met).

While the foregoing cost functions may appear to be more complex than traditional cost functions, those skilled in the art will appreciate that solving the foregoing cost functions is not significantly more computationally challenging than those traditional cost functions. If desired, a chain rule can be applied to perform gradient back-propagation if any line-search approach is used to perform the actual optimization.

Pursuant to the foregoing teachings, there is no need for a user to find weights for some or all of the utilized non-dosimetric parameters. The aforementioned allowance parameters may, at least in many application settings, be readily deduced from an applicable biological model. In any event, these teachings will facilitate, at least in many application settings, a robust automatic approach to planning since the allowance parameters can be applied more universally than typical prior art weights for non-dosimetric parameters.

Those skilled in the art will recognize that a wide variety of modifications, alterations, and combinations can be made with respect to the above-described embodiments without departing from the scope of the invention, and that such modifications, alterations, and combinations are to be viewed as being within the ambit of the inventive concept.

What is claimed is:

1. A method comprising:
by a control circuit configured to optimize an ionizing radiation treatment plan as a function of a plurality of different criteria that include both dosimetric parameters and non-dosimetric parameters:
during a first optimization phase, generating a first phase optimized ionizing radiation treatment plan as a function of dosimetric parameters and a first cost function;
during a second optimization phase, generating a second phase optimized ionizing radiation treatment plan as a function of a second cost function that is based on the first phase optimized ionizing radiation treatment plan and at least one non-dosimetric parameter, and which second cost function is different from the first cost function.

2. The method of claim 1, wherein the dosimetric parameters include dosing information for at least one of a target patient volume and an organ-at-risk.

3. The method of claim 1 wherein the at least one non-dosimetric parameter includes a parameter pertaining to at least one of:
time;
fluence smoothness;
monitor units;
ionizing radiation treatment platform performance;
passing a quality assurance assessment.

4. The method of claim 1, wherein the control circuit is configured to generate the first phase optimized ionizing radiation treatment plan as a function of only dosimetric parameters to the exclusion of any non-dosimetric parameters.

5. The method of claim 1, wherein the control circuit is configured to generate the second phase optimized ionizing radiation treatment plan as a function of the first phase optimized ionizing radiation treatment plan, the at least one non-dosimetric parameter, and at least one dosimetric parameter.

6. The method of claim 5, wherein the at least one dosimetric parameter includes all of the dosimetric parameters that were used during the first optimization phase.

7. The method of claim 1, further comprising:
   during a third optimization phase, generating a third phase optimized ionizing radiation treatment plan as a function of the second phase optimized ionizing radiation treatment plan and at least one non-dosimetric parameter.

8. The method of claim 7, wherein the at least one non-dosimetric parameter used during the third optimization phase is different from the at least one non-dosimetric parameter used during the second optimization phase.

9. The method of claim 1, further comprising:
   determining an allowance parameter for at least one of the dosimetric parameters to provide at least one determined allowance parameter;
   and wherein generating the second phase optimized ionizing radiation treatment plan as a function of the first phase optimized ionizing radiation treatment plan and at least one non-dosimetric parameter comprises generating the second phase optimized ionizing radiation treatment plan as a function of the first phase optimized ionizing radiation treatment plan, the at least one non-dosimetric parameter, and the at least one determined allowance parameter.

10. The method of claim 9, wherein:
   determining an allowance parameter for at least one of the dosimetric parameters to provide at least one determined allowance parameter comprises determining a plurality of allowance parameters for each of a plurality of the dosimetric parameters to provide a plurality of determined allowance parameters;
   and wherein generating the second phase optimized ionizing radiation treatment plan as a function of the first phase optimized ionizing radiation treatment plan and at least one non-dosimetric parameter comprises generating the second phase optimized ionizing radiation treatment plan as a function of the first phase optimized ionizing radiation treatment plan, the at least one non-dosimetric parameter, and the plurality of determined allowance parameters.

11. An apparatus comprising:
   a control circuit configured to optimize an ionizing radiation treatment plan as a function of a plurality of different criteria that include both dosimetric parameters and non-dosimetric parameters by, at least in part:
   during a first optimization phase, generating a first phase optimized ionizing radiation treatment plan as a function of dosimetric parameters;
   during a second optimization phase, generating a second phase optimized ionizing radiation treatment plan as a function of a second cost function that is based on the first phase optimized ionizing radiation treatment plan and at least one non-dosimetric parameter, and which second cost function is different from the first cost function.

12. The apparatus of claim 11, wherein the dosimetric parameters include dosing information for at least one of a target patient volume and an organ-at-risk.

13. The apparatus of claim 11 wherein the at least one non-dosimetric parameter includes a parameter pertaining to at least one of:
   time;
   fluence smoothness;
   monitor units;
   ionizing radiation treatment platform performance;
   passing a quality assurance assessment.

14. The apparatus of claim 11, wherein the control circuit is further configured to:
   generate the first phase optimized ionizing radiation treatment plan as a function of only dosimetric parameters to the exclusion of any non-dosimetric parameters.

15. The apparatus of claim 11, wherein the control circuit is further configured to:
   generate the second phase optimized ionizing radiation treatment plan as a function of the first phase optimized ionizing radiation treatment plan, the at least one non-dosimetric parameter, and at least one dosimetric parameter.

16. The apparatus of claim 15, wherein the at least one dosimetric parameter includes all of the dosimetric parameters that were used during the first optimization phase.

17. The apparatus of claim 11, wherein the control circuit is further configured to:
   during a third optimization phase, generate a third phase optimized ionizing radiation treatment plan as a function of the second phase optimized ionizing radiation treatment plan and at least one non-dosimetric parameter.

18. The apparatus of claim 17, wherein the at least one non-dosimetric parameter used during the third optimization phase is different from the at least one non-dosimetric parameter used during the second optimization phase.

19. The apparatus of claim 11, wherein the control circuit is further configured to:
   determine an allowance parameter for at least one of the dosimetric parameters to provide a determined allowance parameter;
   and wherein the control circuit is configured to generate the second phase optimized ionizing radiation treatment plan as a function of the first phase optimized ionizing radiation treatment plan and at least one non-dosimetric parameter by generating the second phase optimized ionizing radiation treatment plan as a function of the first phase optimized radiation treatment plan, the at least one non-dosimetric parameter, and the at least one determined allowance parameter.

20. The apparatus of claim 11, wherein the control circuit is further configured to:
   determine an allowance parameter for at least one of the dosimetric parameters to provide at least one determined allowance parameter comprises determining a plurality of allowance parameters for each of a plurality of the dosimetric parameters to provide a plurality of determined allowance parameters;
   and wherein the control circuit is configured to generate the second phase optimized ionizing radiation treatment plan as a function of the first phase optimized ionizing radiation treatment plan and at least one non-dosimetric parameter by generating the second phase optimized ionizing radiation treatment plan as a function of the first phase optimized ionizing radiation treatment plan, the at least one non-dosimetric parameter, and the plurality of determined allowance parameters.

* * * * *